United States Patent [19]

Luisoli et al.

[11] Patent Number: 5,229,521

[45] Date of Patent: Jul. 20, 1993

[54] PROCESS FOR THE PREPARATION OF SYMMETRICAL 2,2-METHYLENEBISBENZOTRIAZOLYL PHENOLS

[75] Inventors: Reto Luisoli, Hölstein; Werner Stegmann, Liestal, both of Switzerland

[73] Assignee: Ciba-Geigy Corporation, Ardsley, N.Y.

[21] Appl. No.: 965,560

[22] Filed: Oct. 23, 1992

Related U.S. Application Data

[63] Continuation of Ser. No. 802,781, Dec. 6, 1991, abandoned.

[30] Foreign Application Priority Data

Dec. 11, 1990 [CH] Switzerland ............... 3903/90-9

[51] Int. Cl.$^5$ ............................................. C07D 249/20
[52] U.S. Cl. ................................... 548/260; 548/257; 548/259
[58] Field of Search ..................... 548/260, 257, 259

[56] References Cited

U.S. PATENT DOCUMENTS 4,642,350 2/1987 Davatz et al.
4,681,905 6/1987 Kubota et al. ................ 548/260
4,937,348 6/1990 Kubota ......................... 548/260

Primary Examiner—Marianne M. Cintins
Assistant Examiner—John D. Peabody, II
Attorney, Agent, or Firm—Luther A. R. Hall

[57] ABSTRACT

Compounds of formula

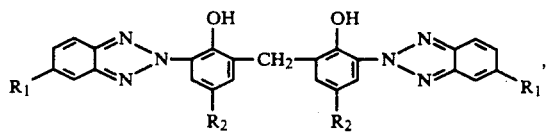

wherein
$R_1$ is hydrogen alkyl, alkoxy, phenyl, phenylaklyl or halogen, and $R_2$ is alkyl phenyl, phenylaklyl or cycloalkyl, are prepared by reacting a compound of formula

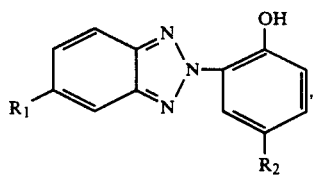

with a compound of formula

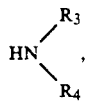

wherein $R_3$ and $R_4$ are alkyl, and formaldehyde, in a one-pot process in the absence of a solvent.

10 Claims, No Drawings

PROCESS FOR THE PREPARATION OF SYMMETRICAL 2,2-METHYLENEBISBENZOTRIAZOLYL PHENOLS

This application is a continuation of U.S. application Ser. No. 07/802,781 filed Dec. 8, 1991, now abandoned.

The present invention relates to a novel process for the preparation of 2,2'-methylenebisbenzotriazolyl phenols.

A process for the preparation of such compounds is disclosed in EP-A-180 993. In this process, a benzotriazolyl phenol is reacted in a first step with an amine and formaldehyde in an organic solvent to give the corresponding Mannich base. In a second step, the isolated Mannich base is reacted with further benzotriazolyl phenol in another organic solvent to give the desired 2,2'-methylenebisbenzotriazolyl phenol.

It has now been found that symmetrical 2,2'-methylenebisbenzotriazolyl phenols are more simply and more rapidly obtainable than heretofore by carrying out the reaction of benzotriazolyl phenol, amine and formaldehyde in the absence of an organic solvent.

Accordingly, the invention relates to a process for the preparation of symmetrical 2,2'-methylenebisbenzotriazolyl phenols of formula

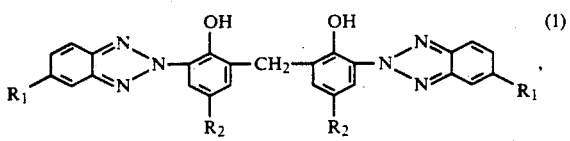

wherein
$R_1$ is hydrogen, alkyl or alkoxy of 1 to 12 carbon atoms, phenyl, phenylaklyl containing 1 to 4 carbon atoms in the alkyl moiety or halogen, and
$R_2$ is alkyl of 1 to 12 carbon atoms which is substituted by $CO_2H$ groups, phenyl, phenylaklyl containing 1 to 4 carbon atoms in the alkyl moiety or cycloalkyl of 5 to 8 carbon atoms, which process comprises reacting a compound of formula

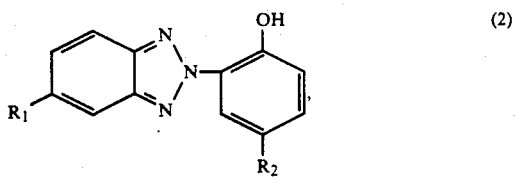

wherein $R_1$ and $R_2$ have the given meanings, with a compound of formula

wherein $R_3$ and $R_4$ are each independently of the other alkyl of 1 to 4 carbon atoms, and with the compound of formula
(4) $CH_2O$, or a polymer thereof, to give the corresponding Mannich base, and treating said Mannich base with a base, both reactions being carried out consecutively in the same reaction vessel without isolation of the intermediate.

The compounds of formula (1) are known, for example for EP-A-180 993 cited above. The starting compounds of formula (2) are are also known and disclosed in U.S. Pat. No. 4,642,350 and EP-A-31 302, with processes for their preparation.

The 2,2'-methylenebisbenzotriazolyl phenols of formula (1) can be used as light stabilisers inorganic polymers.

The substituent $R_1$ in the compounds of formula (1) prepared by the process of this invention is, in addition to hydrogen, alkyl of 1 to 12 carbon atoms, typically methyl, ethyl, propyl, butyl, hexyl, octyl, nonyl, decyl and dodecyl as well as corresponding branched isomers. Examples of suitable alkoxy radicals can be inferred from this recitation. Further, $R_1$ is phenyl or phenylalkyl containing 1 to 4 carbon atoms in the alkyl moiety. Illustrative examples are phenylethyl and phenylpropyl, α-methylbenzyl, α,α-dimethylbenzyl and, preferably, benzyl. $R_1$ may also be halogen, such as chloro or bromo. Preferably $R_1$ is hydrogen, alkyl of 1 to 4 carbon atoms or chloro.

Suitable alkyl radicals $R_2$ are the same as those cited for $R_1$. These alkyl radicals may be substituted by $CO_2H$ groups to form groupings such as $-CH_2CH_2CO_2H$. In addition to phenyl and phenylaklyl containing 1 to 4 carbon atoms in the alkyl moiety (examples as for $R_1$), $R_2$ may also be cycloalkyl of 5 to 8 carbon atoms, typically cyclopentyl, cyclohexyl and cyclooctyl.

$R_3$ and $R_4$ in the compounds of formula (3) are each independently of the other alkyl of 1 to 4 carbon atoms, such as methyl, propyl and butyl, as well as corresponding branched isomers.

It is preferred to use those compounds of formula (2) wherein $R_1$ is hydrogen, alkyl of 1 to 4 carbon atoms or halogen, preferably chloro, and $R_2$ is alkyl of 1 to 12 carbon atoms, and, more particularly, wherein $R_1$ is hydrogen and $R_2$ is alkyl of 6 to 12 carbon atoms. A particularly preferred alkyl radical $R_2$ is tert-octyl.

$R_3$ and $R_4$ in the compounds of formula (3) preferably have the same meaning and are preferably methyl or butyl.

In addition to formaldehyde, it is also possible to use as compound of formula (4) a polymer of formaldehyde, such as paraformaldehyde [$(CH_2O)_n, n=12-30$] or trioxane.

The process of this invention may be carried out, for example, by charging a benzotriazolyl phenol and formaldehyde to the reactor, conveniently under underpressure, typically 1 to 50 mbar, and converting this mixture into a melt. The dialkylamine is passed into this melt and the reaction mixture is then allowed to continue to react at somewhat higher temperature, typically from 120° to 150° C. The pressure in the reactor may rise during this phase to about 1700–1900 mbar. Normally the reaction can be discontinued even after 2 to 4 hours. The melt, which now contains the Mannich base and unreacted benzotriazolyl benzene, is allowed to cool and the water of reaction and excess amine are removed by applying a vacuum. The Mannich base is not isolated and is further reacted in the same reactor. For deamination, a base, for example an alkali metal alcoholate such as sodium methanolate or ethanolate, or an alkali metal hydroxide such as sodium or potassium hydroxide, is added to the reaction mixture, and the batch is heated to about 180° to 220° C. under underpressure, typically 150 to 200 mbar. Normally the deamination is terminated after 2 to 4 hours. To neutralise the base, the melt is taken up in a higher boiling solvent such as xylene, and treated with a carboxylic acid, preferably formic or acetic acid. After clarification by filtration, the reaction product is worked up by conventional methods such as crystallisation, distillation or extraction. The melt crystallisation as working up or purification step can follow directly after the neutralisation with the carboxylic acid. In this case, the addition of the organic solvent is dispensed with. Unreacted benzotriazolyl phenol can be recovered from the higher boiling organic solvent by distillation, for example by means of a thin-film evaporator, whereby the yield, based on consumed benzotriazolyl phenol, usually rises by 4 to 10%. The solvent can be recycled.

Characteristic of the inventive process is that it can be carried out as a one-pot process in the absence of an organic solvent.

In addition to an increase in yield of pure product, this process affords further significant advantages over the prior art process in EP-A-180 933. Compared with this prior art, the process of this invention shortens the total reaction time of 34 hours (24 hours for step 1, 10 hours for step 2) to 4 to 8 hours. This means that the inventive process leads to higher yields of product in only a sixth to an eighth of the time required solely for the first reaction step in EP-A-180 933, without loss of purity of the product. The space-time yield is improved in the practice of this invention by at least the factor 5.

In the practice of this invention, the isolation of the intermediate (Mannich base of formula

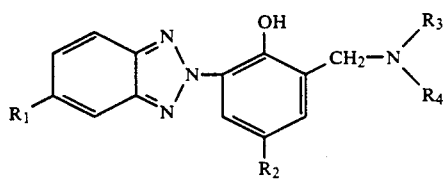

or even the purification of this intermediate, is also unnecessary.

In EP-A-180 933, different organic solvents are used for the first and second reaction steps. The problems associated therewith, i.e. the purification or disposal of the solvent, do not arise in the process of this invention.

These advantages make it clearly apparent that the process of this invention is a simple and very economic method of preparing 2,2'-methylenebisbenzotriazolyl phenols.

It is preferred to carry out the inventive process in the temperature range from 60° to 300° C., preferably from 130° to 220° C. The first step up to the preparation of the Mannich base is carried out at 60° to 150° C., preferably at 120° to 150° C., and the second step up to the formation of the final product is carried out at 180° to 300° C., preferably at 180° to 220° C. It is necessary to carry out the second step in the presence of a base, for example of an alkali metal alcoholate or alkali metal hydroxide. The molar ratios of the compounds of formulae (2), (3) and (4) is preferably 2:1:1 to 2:3:3, more particularly 2:2.5:1.5.

The process of this invention is especially suitable for the preparation of 2,2'-methylenebis[4-(1,1,3,3-tetramethylbutyl)-6-benzotriazolylphenol] by reacting the compound of formula (2), wherein $R_1$ is hydrogen and $R_2$ is tert-octyl, with a compound of formula (3), wherein $R_3$ and $R_4$ are simultaneously methyl or butyl, and formaldehyde, which compounds are used in the molar ratio of 2:2:1 to 2:2.2:1.1, and the reaction temperature is the the range from 130° to 220° C.

The invention is illustrated in more detail by the following Examples in which percentages are by weight.

EXAMPLE 1

A 0.75 l double-jacket flask, tested to 1.5 bar overpressure, and equipped with gas inlet tube, descending cooler with receiving flask and vacuum connecting tube with cooling trap to the vacuum pump, is charged with 323.2 g (1.0 mol) of 4-(1,1,3,3-tetramethyl)butyl-6-benzotriazolyl-2-yl phenol and 16.5 g (0.55 mol) of paraformaldehyde. After evacuating the flask to 20 mbar and closing it, the mixture is fused at a jacket temperature of 120° C. whereupon the pressure rises to about 270 mbar. Then 24.8 g (0.55 mol) of gaseous dimethylamine are introduced into the readily stirrable melt at 100°-105° C. over 30 minutes. The final pressure rises to 900-1000 mbar. The reaction mixture is heated to 135° C. and stirred at this temperature for 2 to 4 hours, the pressure rising to 1800 mbar. After cooling to 90° C., the water of reaction, together with unreacted amine, is removed by applying a vacuum and heating to 130° C. The pressure is released with nitrogen and then 2.2 g (0.04 mol) of sodium methylate are added as catalyst to the reaction mass which, after applying a vacuum of 200 mbar, is heated rapidly to 200° C. From about 145°-155° C., the splitting off of dimethylamine is observed. After stirring for 2 to 4 hours at 200° C. and about 200 mbar, the deamination ceases and the reaction is complete. After dissolving the melt in 200 g of a xylene mixture, the alkaline catalyst is neutralised with 3.2 ml of formic acid (85%), the solution is clarified by filtration at 130° C. and the filtrate is washed with 75 g of a xylene mixture. Crystallisation is effected by cooling to about 0° C. The viscous suspension is filtered with suction, washed with 100 g of a xylene mixture, and the product is dried in a vacuum drying oven at 120° C. Yield: 294 g of product in the form of a yellowish powder (89.3% of theory, based on consumed benzotriazolyl phenol), m.p. 197.6° C., transmission (5% in chloroform) at 450 nm: 96.4%, at 500 nm: 97.7%).

The washing liquor can be completely concentrated by evaporation and the residue distilled on a thin-film evaporator such that the unreacted benzotriazolyl phenol can be recovered in quantitative yield. In this way 4 to 10% of unreacted benzotriazolylphenol can be recovered and used in the next batch. The yield, based on consumed benzotriazolylphenol, is thus 90-92% of theory.

EXAMPLE 2

A 0.75 l sulfonation flask equipped with anchor stirrer, reflux condenser, nitrogen inlet and oil bath is charged with 323.2 g (1.0 mol) of 4-(1,1,3,3-tetramethyl)butyl-6-benzotriazolyl-2-yl phenol and 16.5 g (0.55 mol) of paraformaldehyde together with 142.2 g (1.1 mol) of dibutylamine. The suspension is heated to about 100° C. and stirred for 6 hours at 100°-102° C. Excess dibutylamine and the water of reaction are removed by distillation at 5 mbar and 120° C. Subsequent working up is effected as described in Example 1, but under a pressure of 5 mbar and the reaction time is only 1 to 2 hours.

Yield: 227-290 g of product in the form of a yellowish powder (84-88% of theory, based on benzotriazolyl phenol; m.p. 197° C. transmission 5% in chloroform) at 450 nm: 97.0%, at 500 nm: 98.8%).

The mother liquor can be worked up as in Example 1. The yield then rises to 88'92% of theory.

EXAMPLE 3

The 0.75 l double-jacket pressure reactor of Example 1 is charged with 323.2 g (1.0 mol) of 4-(1,1,3,3-tetramethyl)butyl-6-benzotriazol-2-yl phenol, 15.6 g (0.52 mol) of paraformaldehyde and 134.4 g (1.04 mol) of dibutylamine. The reactor is evacuated to 100 mbar and closed. The suspension is heated to 135° C. and stirred for 1 hour at this temperature, the pressure rising to about 1.7 bar. The further steps are carried out in accordance with the general procedure described in Example 1, except that the amount of catalyst is reduced to 0.01 mol, corresponding to 0.54 g or 1 mol %.

Yield: 277 to 290 g of product in the form of a yellowish powder (84 to 88% theory, based on the benzotriazolyl phenol used, or 88 to 92%, based on consumed benzotriazolyl phenol, m.p: 197.5° C., transmission (5% in chloroform) at 450 nm: 97.9% at 500 nm: 99.4%).

What is claimed is:

1. An improved process for the preparation of a symmetrical 2,2'-methylenebisbenzotriazolyl phenol of formula

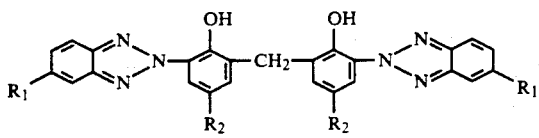

wherein
$R_1$ is hydrogen, alkyl or alkoxy of 1 to 12 carbon atoms, phenyl, phenylaklyl containing 1 to 4 carbon atoms in the alkyl moiety or halogen, and $R_2$ is alkyl of 1 to 12 carbon atoms, alkyl of 1 to 12 carbon atoms which is substituted by $CO_2H$ groups, phenyl, phenylaklyl containing 1 to 4 carbon atoms in the alkyl moiety or cycloalkyl of 5 to 8 carbon atoms, which process comprises reacting a compound of formula

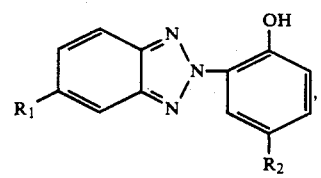

wherein $R_1$ and $R_2$ have the meanings defined above, with a compound of formula

wherein $R_3$ and $R_4$ are each independently of the other alkyl of 1 to 4 carbon atoms, and with the compound of formula

or a polymer thereof, to give the corresponding Mannich base, and treating said Mannich base with a base, both reactions being carried out consecutively in the same reaction vessel without isolation of the intermediate, wherein the improvement comprises
carrying out the reaction in the melt and in the absence of an organic solvent.

2. A process according to claim 1, wherein $R_1$ is hydrogen, alkyl of 1 to 4 carbon atoms or halogen, and $R_2$ is alkyl of 1 to 12 carbon atoms.

3. A process according to claim 2, wherein $R_1$ is hydrogen and $R_2$ is alkyl of 6 to 12 carbon atoms.

4. A process according to claim 3, wherein $R_2$ is tert-octyl.

5. A process according to claim 1, wherein $R_3$ and $R_4$ are methyl or butyl.

6. A process according to claim 1, wherein the reaction is carried out in the temperature range from 60° C. to 300° C.

7. A process according to claim 1, wherein the compounds of formulae (2), (3) and (4) are reacted in the molar ratio of 2:1:1 to 2:3:3.

8. A process for the preparation of 2,2'-methylenebis[4-(1,1,3,3-tetramethylbutyl)-6-benzotriazolylphenol] according to claim 1 by reacting the compound of formula (2), wherein $R_1$ is hydrogen and $R_2$ is 4-(1,1,3,3-tetramethylbutyl), with a compound of formula (3), wherein $R_3$ and $R_4$ is methyl or butyl, and formaldehyde, in the molar ratio of 2:2:1 to 2:2.2:1.1, and in the temperature range from 130° C. to 220° C.

9. A process according to claim 6 wherein the temperature range is from 130° C. to 220° C.

10. A process according to claim 7 wherein the molar ratio is 2:1:1 to 2:2.5:1.5.

* * * * *